United States Patent

Pfeiffer et al.

[11] Patent Number: 5,526,817
[45] Date of Patent: Jun. 18, 1996

[54] PROCESS FOR DETERMINING A PATIENT'S CIRCULATORY FILL STATUS

[75] Inventors: Ulrich Pfeiffer; Reinhold Knoll, both of München, Germany

[73] Assignee: Pulsion Verwaltungs GmbH & Co. Medizintechnik KG, Germany

[21] Appl. No.: 325,347

[22] PCT Filed: Apr. 30, 1993

[86] PCT No.: PCT/EP93/01052

§ 371 Date: Oct. 31, 1994

§ 102(e) Date: Oct. 31, 1994

[87] PCT Pub. No.: WO93/21823

PCT Pub. Date: Nov. 11, 1993

[30] Foreign Application Priority Data

Apr. 30, 1992 [DE] Germany .................. 42 14 402.7

[51] Int. Cl.$^6$ ......................................... A61B 5/00
[52] U.S. Cl. .................. 128/691; 128/668; 128/692; 128/713
[58] Field of Search ................... 128/668, 670, 128/691, 692, 713, 736

[56] References Cited

U.S. PATENT DOCUMENTS

| 4,858,618 | 8/1989 | Konno et al. ............. | 128/713 |
| 5,046,502 | 9/1991 | Kunig .................... | 128/670 |

FOREIGN PATENT DOCUMENTS

| 0060546 | 9/1982 | European Pat. Off. ........ | 128/691 |
| 8102512 | 9/1981 | WIPO ..................... | 128/691 |
| 9305704 | 4/1993 | WIPO ..................... | 128/691 |

OTHER PUBLICATIONS

Database Inspec, IEEE, London, G.B. Inspec No. 4031387 Computers in Cardiology, 19–22, Sep. 1989, C. Vasanelli et al "Quantitative angiographic identification of Functional ventricular aneurysms," see abstract.

Lewis and Pfeiffer, "Practical Applications of Fiberoptics in critical care monitoring" 1990, Springer–Verlag, Berlin pp. 114–125.

C. Vassanelli, "Quantitative Angiographic Identification of Functional Left Ventricular Aneurysms," Abstract, *Proceedings on Computers in Cardiology*, 1989.

Primary Examiner—Angela D. Sykes
Assistant Examiner—Robert L. Nasser, Jr.
Attorney, Agent, or Firm—Sixbey, Friedman, Leedom & Ferguson; David S. Safran

[57] ABSTRACT

A process and a device for determining a patient's circulatory fill status, particularly the global end-diastolic volume of the heart (GEDV), intrathoracic blood volume (ITBV), pulmonary blood volume (PBV), extravascular lung water volume (EVLW), and/or global cardiac function index (CFI) by means of thermo-dilution; with this process intrathoracic thermo-volume (ITTV) and pulmonary thermo-volume (PTV), for example, are obtained and the global end-diastolic volume of the heart (GEDV) is determined from the equation

GEDV=ITTV–PTV.

The other volumes can be calculated by means of this parameter, which is specific for the fill status of the heart, as well as other species-specific characteristics (a, a', b, b').

28 Claims, 4 Drawing Sheets

ITTV = EDV(RA+RV+LA+LV) + PTV

GEDV = ITTV − PTV = EDV(RA+RV+LA+LV)

PROCESS FOR DETERMINING A PATIENT'S CIRCULATORY FILL STATUS

BACKGROUND OF THE INVENTION

The invention relates to a process for determining a patient's circulatory fill status, particularly the global end-diastolic volume GEDV, intrathoracic blood volume ITBV, pulmonary blood volume PBV, extravascular lung water EVLW, and/or global cardiac function index CFI; with this process the intrathoracic thermo-volume ITTV and pulmonary thermo-volume PTV are determined by means of thermo-dilution. The term "circulatory fill status" as used herein encompasses the fill statu of any part of a patient's circulatory system.

In the critical-care diagnosis and treatment of extremely sick patients, cardiac output C. O. and circulatory fill volume are important characteristics.

A pulmonary catheter is currently in wide use; it can be used to measure cardiac output C. O. by the thermo-dilution process and, as parameters for circulatory filling, to measure central venous pressure CVP, right ventricular end-diastolic volume RVEDV, and pulmonary-capillary wedge pressure PCWP. In this connection see D. Payen "Physiological Determinants of Hemodynamic Parameters" from "Strategy in Bedside Hemodynamic Monitoring," published by J.-F. Dhainaut and D. Payen, Springer-Verlag, 1991, pp. 28–35.

Measuring the pressures CVP and PCWP against atmospheric pressure has the decisive disadvantage that it is not possible to derive the circulating volume from these values reliably. In addition, the values CVP and PCWP, which are often referred to as circulatory fill pressures, are not very sensitive to changes in volume. In this connection see U. J. Pfeiffer et. al. "Sensitivity of Central Venous Pressure, . . . " from F. R. Lewis and U. J. Pfeiffer "Practical Application of Fiberoptics in Critical Care Monitoring," Springer-Verlag, 1990, pp. 25–31.

Because this was realized, the measurement of the RVEDV value was introduced, but this value is indicative only of the fill volume of one of the four ventricles. Moreover, there is a considerable degree of variation in the determination of the RVEDV value. In this connection see J.-F. Dhainaut et al. "Validity and Clinical Applications of Fast Response Thermistor for Right Ventricular Ejection Fraction Monitoring," from J.-F. Dhainaut and D. Payen: "Strategy in Bedside Hemodynamic Monitoring," Springer-Verlag, 1991, pp. 59 ff.

A more specific process for measuring cardiac output C. O. and circulatory fill volume is the so-called thermo-dye technique. This technique is a combination of dye dilution DD and thermo-dilution TD and makes the intrathoracic blood volume ITBV available as a specific parameter for circulatory filling. The value encompasses the right-atrial end-diastolic volumes RAEDV and right-ventricular end-diastolic volume RVEDV, the blood volume of the lungs (pulmonary blood volume) PBV, and the end-diastolic volumes of the left atrium LAEDV and left ventricle LVEDV. This process has the further advantage that the extravascular water of the lung EVLW can also be determined. In this connection see U. J. Pfeiffer et al. "A Fiberoptics-Based System . . . " in U. J. Pfeiffer "Practical Application of Fiberoptics in Critical Care Monitoring," Springer-Verlag, 1990, pp. 115 ff.

The thermo-dye process has the disadvantage, however, that it requires the injection of a relatively expensive dye, in which connection, because of its sensitivity to light and heat, the injectable dye solution always has to be made up right before the injection, i.e., at least once a day. In addition, the dye may cause allergic or anaphylactic reactions.

The fiber-optic thermistor catheter used in this process is very expensive as a disposable item. Moreover, the corresponding measurement device is also relatively expensive due to the fact that a reflection photometer is used to measure the dye concentration.

Fiber-optic dye measurement may also be impaired by problems with optical measurement, e.g., due to deposits on the optical eye of the measurement catheter, dislocation of the measurement catheter, etc. Finally, because of the size of the fiber-optic thermistor catheter, thermodye dilution measurement can be done only in the femoral artery. The measurement catheter sizes that have been common to date make it completely impossible to take measurements on children or infants.

SUMMARY OF THE INVENTION

The object of the invention is thus to indicate a process of the type mentioned in the introduction, with the aid of which circulatory fill status can be determined without dye dilution, using only thermo-dilution.

According to the invention, this object is accomplished by deriving a parameter GEDV which reflects the sum of the ventricle volumes without the lung volume from a thermo-dilution curve.

The process of the invention is thus based on deriving from the thermo-dilution curve a parameter which represents the sum of smaller mixing volumes, without the largest mixing volume. These volumes essentially correspond to the end-diastolic cardiac volumes. The corresponding parameter is therefore called the global end-diastolic volume (GEDV) for short. The GEDV can be determined from, e.g., the difference between the total mixing volume ITTV and the largest mixing volume PTV or as a function of the appearance time AT. In connection with other results from analyzing the thermo-dilution curve and species-specific relationships, it is then possible to obtain other parameters for assessing the circulatory system.

A device for implementing the process of the invention, as well as particularly preferred designs and implementations of such a device, are also subjects of the present invention. Such a device involves a thermo-dilution measurement arrangement which comprises a thermo-dilution injector, a temperature sensor, and a control and analysis until at which the output values from the temperature sensor and other measurement parameters are available and which generates the intrathoracic thermo-volume (ITTV) and pulmonary thermo-volume (PTV) from the thermo-dilution curve, wherein the analysis device features a difference until at which the generated ITTV and PTV values are available and whose output value is the global end-diastolic volume of the heart (GEDV).

Below, the known thermo-dye process, as well as particularly preferred embodiments of the process of the invention and the device of the invention are described in greater detail, with reference to the corresponding attached drawings.

BRIEF DESCRIPTION OF THE PREFERRED EMBODIMENTS

DETAILED DESCRIPTION OF THE PREFERRED EMBODIMENT

In practice, with the thermo-dye process, a chilled indocyanine green solution is injected into the central venous vascular system. Since the dye indocyanine green immediately binds with plasma proteins, it stays in the circulatory system at least during the first passage from the heart to the lung (intravasal marker). Initially the cold that is introduced, like the dye, is transported from the right ventricle into the lung. There, however, through heat diffusion, the cold can also penetrate into the tissue surrounding the pulmonary capillaries. The cold thus spreads in the intravascular and extravascular spaces in the lung (a so-called extravasal marker). From the lung, the cold flows to the left ventricle more slowly than the dye because of the larger diffusion volume in the lung. The dye and thermo-dilution curves are recorded in the femoral artery by means of a fiber-optic thermistor catheter in the arterial vascular system (see FIG. 2 in this connection).

Figure 3:
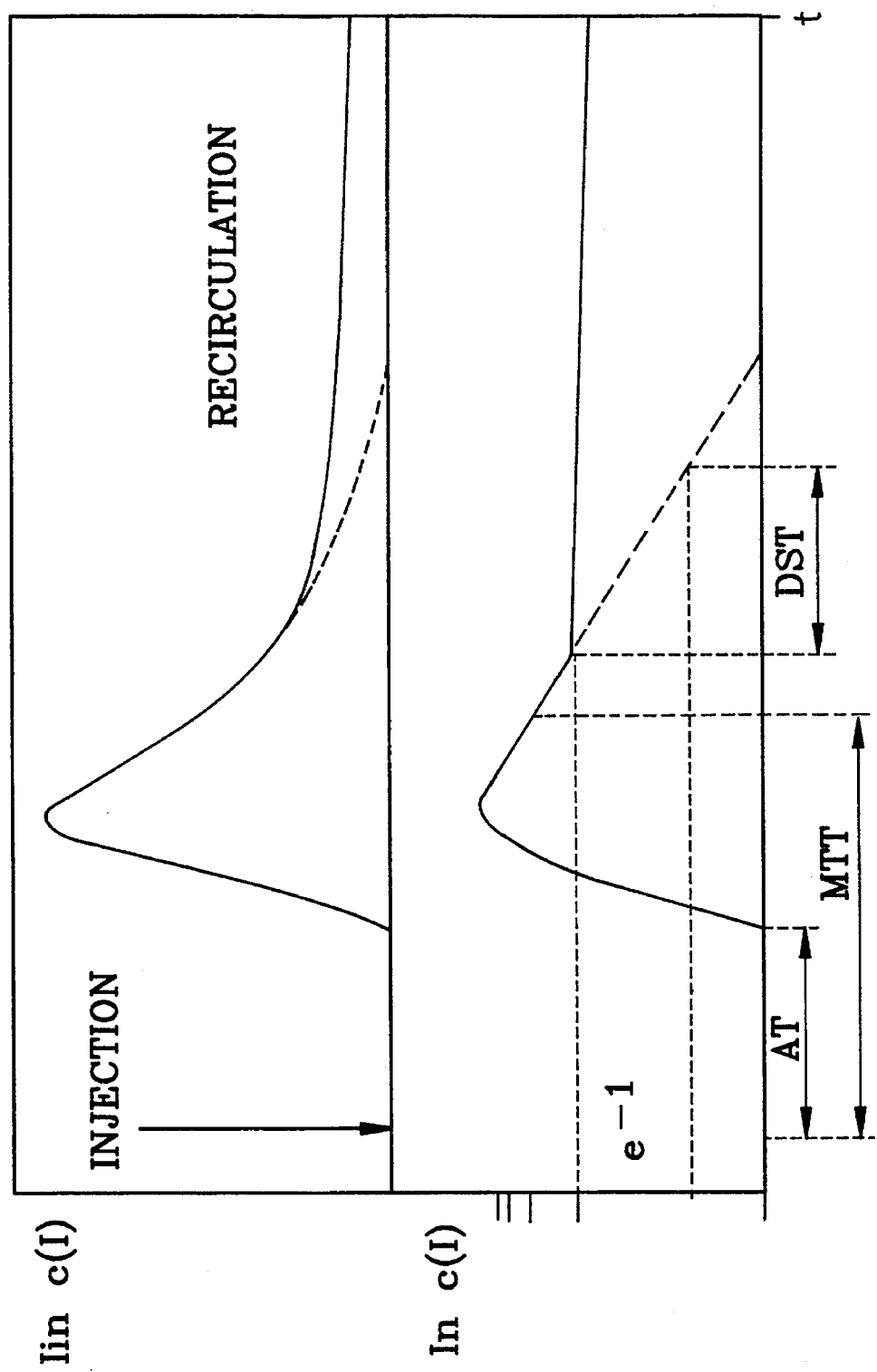
FIG. 3 shows the characteristic plots of the dilution curves that are used for determining the desired volume values, particularly the thermodilution curves.
Figure 4:
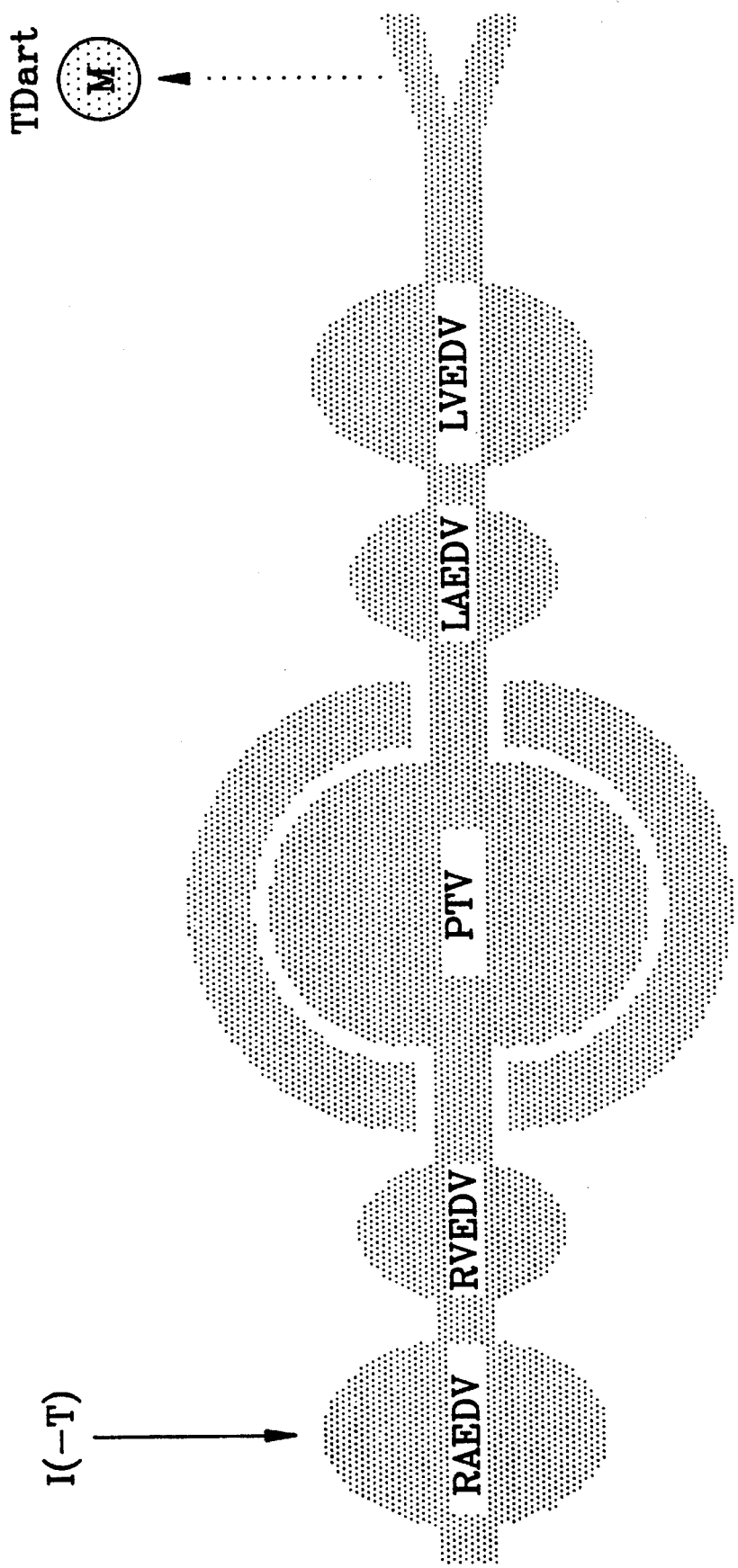
FIG. 4 shows a schematic view of the different values that are to be determined, according to the process of the invention.

The cardiac output C. $O_{\cdot TDart}$, appearance time AT, mean transit time $MTT_{TDart}$, and exponential decay time $DST_{TDart}$ are calculated from the arterial thermo-dilution curve TD. The notation $TD_{art}$ identifies the specific parameter as obtained from the arterial thermo-dilution curve. Only the time parameters $MTT_{DDart}$ and $DST_{DDart}$ are determined from the arterial dye dilution curve. The notation $DD_{art}$ identifies these parameters as obtained from the arterial dye-dilution curve. These curves are depicted in FIG. 3.

The standard Stewart-Hamilton formula, in its adaptation for thermodilution, is used to calculate cardiac output C. O. The standard Stewart-Hamilton formula calculates cardiac output as follows:

$$C.O. = \frac{m(I)}{\int c(I)dt} \quad \text{(Eq. 1)}$$

$$C.O. = \frac{V_1 * (T_B T_I) * K}{\int \Delta T dt} \quad \text{(Eq. 2)}$$

and m(I)=amount of indicator solution c(I)=concentration of indicator solution $V_I$=volume of injection $T_B$=blood temperature $T_I$=temperature of injected substance K=correlation factor for specific weight and specific heat of the injected substance and of the blood T=blood temperature t=time.

Equation 2 (Eq. 2) is the thermo-dilution adapted standard Stewart-Hamilton formula.

Figure 2:
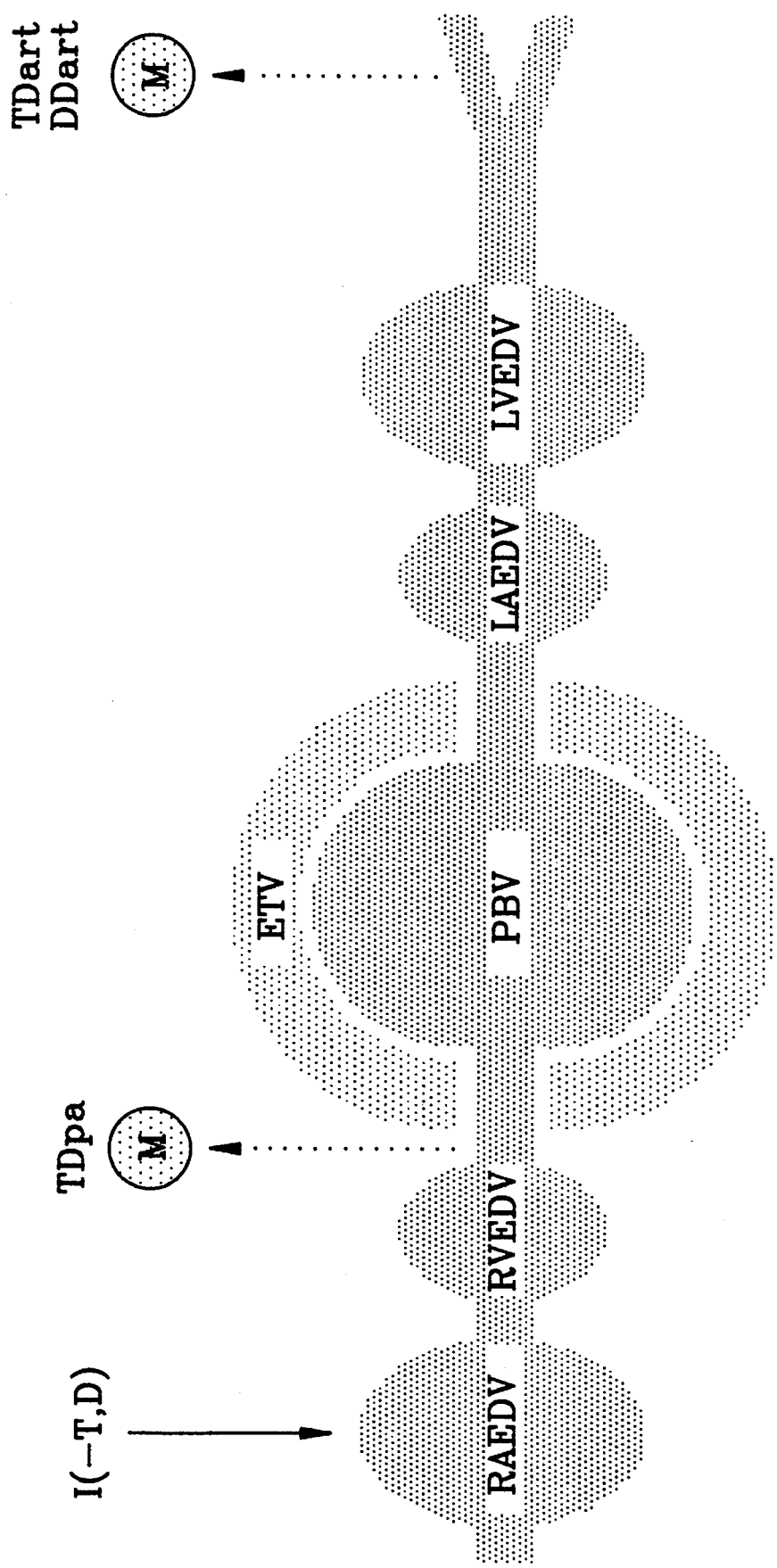
FIG. 2 shows a schematic view of the various values that are to be determined, according to the state of the art.

With respect to indicator dilution, the human cardio-pulmonary system represents a set of individual mixing volumes connected in series, as FIG. 2 indicates schematically. The total volume through which an indicator passes is calculated from the product of cardiac output C. O. and mean transit time MTT. The volume of the largest mixing chamber is indicated by the product of C. O. and DST.

The arterial thermo-dilution curve can be used to determine the intrathoracic thermo-volume ITTV and pulmonary thermo-volume PTV since the lung represents the largest mixing volume for the cold from the injected substance:

$$ITTV = C.~O._{TDart} \times MTT_{TDart}$$

$$PTV = C.~O._{TDart} \times DST_{TDart}$$

The intrathoracic blood volume ITBV and pulmonary blood volume PBV can be calculated from the arterial dye dilution curve since the largest mixing volume for the dye lies in the pulmonary vascular system:

$$ITBV = C.~O._{TDart} \times MTT_{DDart}$$

$$PBV = C.~O._{TDart} \times DST_{DDart}$$

According to findings in the literature, the extravascular lung water volume EVLW can be equated with the extravascular cold dispersion volume in the lung ETV. EVLW can be calculated from ETV in two ways:

$$EVLW = ETV_{MTT} = ITTV - ITBV$$

and $$EVLW = ETV_{DST} = PTV - PBV.$$

Figure 1:
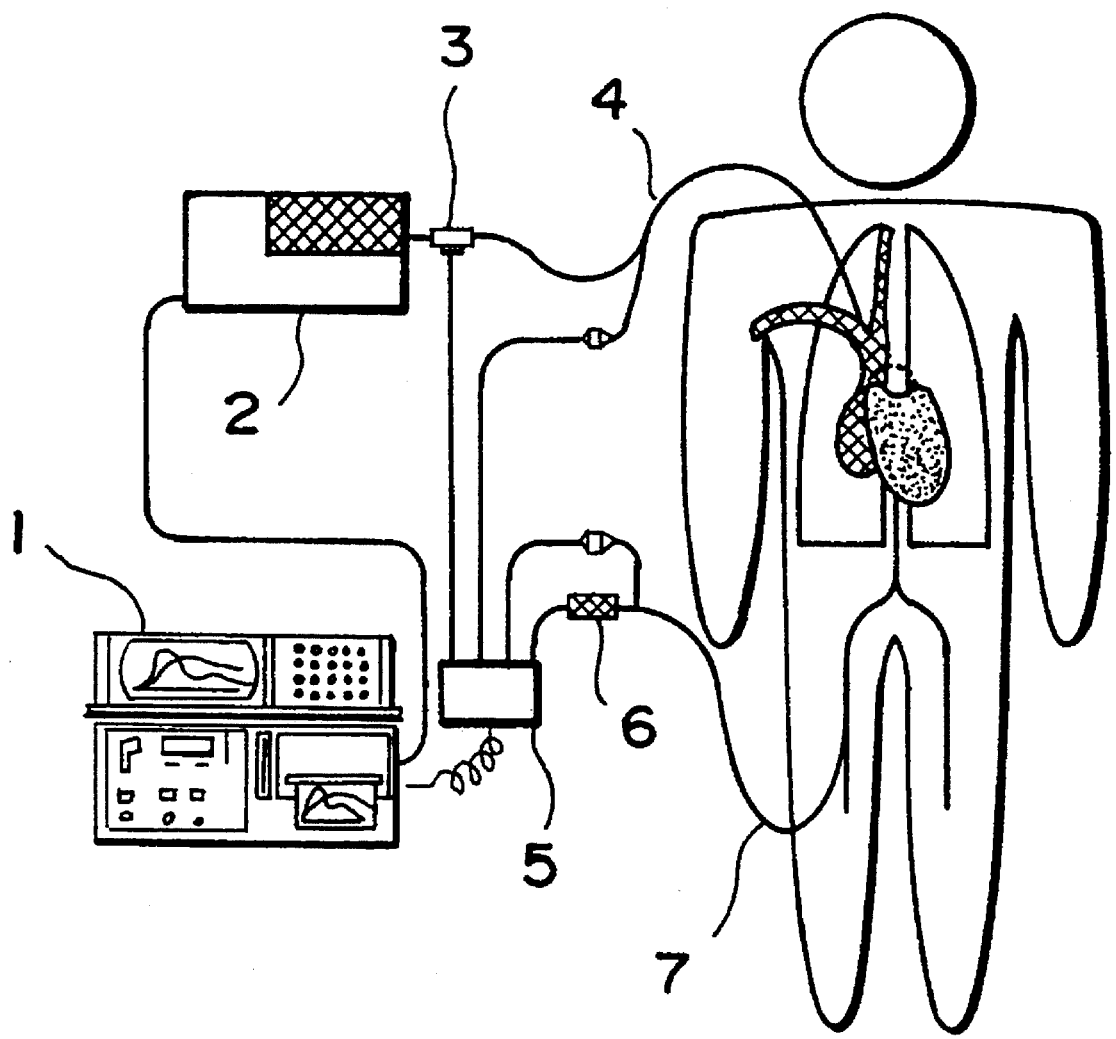
FIG. 1 shows a schematic view of a conventional measurement arrangement for implementing the thermo-dye process.

A conventional measurement arrangement for the thermo-dye process is shown in FIG. 1. Such a measurement arrangement is marketed, for example, under the name COLD Z-021 by Siemens AG, of Erlangen. See the attached specifications sheet for further details. As FIG. 1 indicates, in addition to above-mentioned COLD Z-021 system 1 the overall measurement arrangement encompasses a thermo-dilution injector 2, a temperature sensor 3, a pulmonary-artery catheter 4, a distributor 5, an optical module 6, and a femoral-artery fiber-optic thermistor catheter 7.

Ordinarily a pulmonary catheter and a femoral-artery fiber-optic thermistor catheter are inserted. The chilled dye solution is injected either by hand or by means of an injection machine after a measurement on the measurement device has been initiated by depressing a key. During the injection the temperature of the injected substance is measured by means of the injected-substance temperature sensor. By means of the fiber-optic thermistor catheter placed in the patient's artery, the measurement device records the dye-dilution and thermo-dilution curves. The values for C. O., ITTV, PTV, ITBV, PBV, $ETV_{MTT}$, and $ETV_{DST}$ are determined using the above-described equations. Error detection is accomplished by determining the $ETV_{DST}$ value. A measurement error is signaled if $ETV_{MTT}$ and $ETV_{DST}$ do not agree within specified limits.

With the process of the invention, in contrast to the thermo-dye process, the desired values are determined by means of thermo-dilution alone, without measuring dye dilution.

To do this, before the cold liquid is injected, the time plot of the base blood temperature is determined. From this the base line for the thermo-dilution curve is extrapolated using the least error squares method. Alternatively, the plot of the base blood temperature can also be used toward the end of the measurement to determine the base line.

The base line is determined in order to correct for errors, e.g., noise errors, and to exclude influences arising from variations of physiological origin such as body regulation processes, fever, etc., as well as inaccuracies in the infusion arrangement.

The analysis is no longer initiated by depressing a button; rather, it is done automatically by analyzing the output signal of an injected-substance flow sensor. The time plot of this output signal is used to determine whether an injection is present and how uniform the injection needs to be for the purposes of the measurement. The flow sensor can also be an injected-substance temperature sensor, corresponding to temperature sensor 3 in FIG. 1 if it is designed to warm up when the injected substance is stationary. This can be done by adapting to the ambient temperature, for example to room temperature or body temperature, or by warming the sensor up using the measurement current. For this purpose, the sensor has a small thermal capacity and an adequately reproducible, extremely short reaction time and, when an injection is made, it initially delivers a signal that drops off exponentially, and then rises exponentially after the injection is completed.

In order to determine the mean transit time MTT, the point in time when the injection is made has to be determined precisely.

It is assumed that the examiner can do the indicator injection smoothly; this injection usually consists of 10 ml of ice-cold glucose solution. When an injection machine is used, a smooth injection is virtually guaranteed. The injected-substance temperature curve plotted during the injection is checked for shape. The measurement is discarded if the curve is irregular, i.e., if it has, for example, two or more valleys. If the criteria for a correct injection are met, then the beginning and ending points of the injection, as well as the temperature minimum are determined from the time plot of the injected-substance temperature. If the sensor is designed properly, the temperature plot will consist of an exponential temperature drop down to the minimum temperature starting at the point when the injection begins and an exponential temperature rise starting at the point when the injection ends. Here the time constant of the temperature drop depends on the flow rate and sensor design. This provides two points in time from which the duration of the injection can be determined.

Since theoretically a bolus injection, which cannot be implemented in practice, is assumed, a corrected injection time, i.e., a starting time for the analysis of the mean transit time MTT, is generated from the beginning and ending times of the injection. In the first approximation this corrected injection time will lie, e.g., in the middle between the starting and ending times of the injection. Then the values for C. O., ITTV, and PTV are determined from this time in the way described above, which is basically known already.

The global end-diastolic volume of the heart $GEDV_{TDart}$ is determined from the recorded arterial thermo-dilution curve as a new parameter, one which is specific for the fill status of the heart, from the following equation:

$$GEDV_{TDart} = ITTV_{TDart} - PTV_{TDart}.$$

The global end-diastolic volume of the heart $GEDV_{ATTDart}$ can also be determined from the following equation:

$$GEDV_{AT\ TDart} = a \times AT-VOL_{TDart} + b$$

where $$AT-VOL_{TDart} = C.\ O._{TDart} \times AT_{TDart}$$

and

C. $O._{TDart}$ is cardiac output;
$AT_{TDart}$ is appearance time; and
a, b are species-specific characteristics.

The characteristics a, b can be determined by comparing the GEDV value obtained by another known process, e.g., the thermo-dye process, with the $AT-VOL_{TDart}$ value determined for the species in question.

These values lie between 1.0 and 3.0 ml for a and between ±20% of the normal ITBV value (for man, it is about 900 ml/m$^2$ of body surface) for b.

For man, these characteristics lie at about a= 2.0 and b =—200, where the unit of measure is ml.

The intrathoracic blood volume $ITBV_{TDart}$ can then be determined from the following equation:

$$ITBV_{TDart} = a' \times GEDV_{TDart} + b',$$

where a' and b' are also species-specific characteristics that lie between 1.0 and 2.0 for a' and ±15% of the normal ITBV value[b' . For man, a' = 1.22 and b' = 109 (n=89), and for pigs, a'=1.33 and b'= 13.3 (n=145), where the unit of measure is ml. As in the case of the values a, b, these values are determined by comparison with values obtained by another process.

This generally means that there is a species-specific relationship between $ITBV_{TDart}$ and $GEDV_{TDart}$. Individual and illness-induced differences can be ignored in this regard.

The pulmonary blood volume $PBV_{TDart}$ is then found from the arterial thermo-dilution curve as:

$$PBV_{TDart} = ITBV_{TDart} - GEDV_{TDart}.$$

The extravascular lung water volume $EVLW_{TDart}$ can then be determined from the arterial thermo-dilution curve according to one of the following equations:

$$EVLW_{TDart} = ETV_{MTT\ TDart} = ITTV_{TDart} - ITBV_{TDart} \text{ and } EVLW_{TDart} = ETV_{DST\ TDart} = PTV_{TDart} - PBV_{TDdart}$$

Finally, the global cardiac function index CFI is obtained as another new parameter, as follows:

$$CFI_{TDart} = C.\ O._{TDart} / GEDV_{TDart}.$$

To implement the process of the invention, a single arterial thermodilution catheter can be used which has a small, electrically insulated thermistor at its distal tip and may also feature a lumen for taking blood and measuring arterial blood pressure. This catheter can be made small enough to be readily inserted into the radial artery.

Because of the considerably simpler equipment used, the above-described measurement process of the invention is less expensive than the known thermo-dye process. It represents a simple method that works without expensive equipment and, in particular, without a pulmonary catheter. Because of the measurement catheters, which are simple and can be made small, the process can be used wherever there is central venous access for injecting the indicator and, at the same time, arterial access for measuring temperature.

As a rule the injection can be made via a central-venous catheter, and the insertion of the temperature probe can be done via a radial-artery catheter.

The attached measurement and analysis device is designed in such a way as to have the computation elements required for determining the desired values according to the above-presented equations and can be designed and/or programmed in the form of a microprocessor.

We claim:

1. A process for determining a specific species of patient's circulatory fill status-related parameters by calculating cardiac output according to the standard Stewart-Hamilton formula adapted for thermo-dilution measurement comprising the steps of:

(a) placing a measurement device in the patient's artery;

(b) injecting over a period of time an injectable comprising a cold solution into the patient's circulatory system;

(c) recording an arterial thermo-dilution curve TD with said measurement device and calculating an appearance time AT from said arterial thermo-dilution curve; and (d) deriving a thermo-dilution measurement curve from said injected injectate according to equation (I) to determine a value for GEDV $_{AT\ TDart}$ which reflects a sum of heart ventricle volumes without lung volume:

$$GEDV_{AT\ TDart} = a \times AT\text{-}VOL_{TDart} + b \quad (I)$$

where AT-VOL$_{TDart}$ = C. O.$_{TDart} \times AT_{TDart}$ and GEDV$_{AT}$ TDart = global end-diastolic volume of the heart C. O.$_{TDart}$ = cardiac output AT$_{TDart}$ = appearance time a,b = species specific characteristics determined by comparing the value of GEDV determined by another process with the value of VOL$_{TDart}$ for the specific species of patient.

2. Process according to claim 1, wherein the specific species of patient is a human and a= 2.0 and b = −200.

3. Process according to claim 1, including the step of obtaining a value of a parameter ITBV which reflects intrathoracic blood volume from the equation:

$$ITBV_{TDart} = a'[*] \times GEDV_{TDart} + b'$$

where GEDV$_{TDart}$ is the global end diastolic volume and a' and b' are species specific characteristics that are determined by determining the value of ITBV$_{TDart}$ for each particular species by another process and comparing the value of GEDV$_{TDart}$ obtained with the determined value of ITBV$_{TDart}$ for the specific species of the patient.

4. Process according to claim 3, wherein when the specific species of patient is a human and a' =1.22 and b' = 109.

5. Process according to claim 3, including the step of obtaining a value of a parameter PBV$_{TDart}$ which reflects pulmonary blood volume from the equation:

$$PBV_{TDart} = ITBV_{TDart} - GEDV_{TDart}$$

6. Process according to claim 5, including the step of obtaining a value of a parameter EVLW$_{TDart}$ which reflects extravascular lung water volume from the equation:

$$EVLW_{Tdart} = PTV_{Tdart} - PBV_{Tart}$$

where PTV$_{Tdart}$ is pulmonary thermo-volume calculated from said arterial thermo-dilution curve.

7. Process according to claim 3, wherein the specific species of patient is a pig and a' = 1.33 and b' = 13.3.

8. Process according to claim 1, including the steps of determining a value of a parameter CFI$_{TDart}$ which reflects a global cardiac function index from the equation:

$$i\ CFI_{TDart} = C.\ O.T_{Dart}/GEDV_{TDart}.$$

9. Process according to claim 1, wherein the recording of said arterial thermo-dilution curve of step (c) is initiated based on a flow rate of the cold solution injected.

10. Process according to claim 1, wherein a starting time for said process is determined from starting and ending times of the cold solution injection.

11. Process according to claim 1, including the steps of determining a time plot of base blood temperature and from the time plot extrapolating a base line for the thermo-dilution curve of step (c).

12. Process for determining a patient's circulatory fill status-related parameters using thermo-dilution measurement, including the steps of placing a measurement device in and injecting a cold solution into a patient's circulatory system, deriving a value of a parameter ITTV$_{TDart}$ which reflects intrathoracic thermo-volume and a value of a parameter PTV$_{TDart}$ which reflects pulmonary thermo-volume from an arterial thermo-dilution measurement curve of the cold solution injected into the patient's circulatory system according to the equations:

$$ITTV_{TDart} = C.\ O._{TDart}[*] \times MTT_{TDart}$$

$$PTV_{TDart} = C.\ O._{TDart}[*] \times DST_{TDart}$$

where C. O.$_{TDart}$ is cardiac output determined according to the thermodilution adapted standard Stewart-Hamilton formula $$C.O. = \frac{V_1 * (T_B T_I) * K}{\int \Delta T dt}$$

and V$_I$ = volume of injection

T$_B$ = blood temperature

T$_I$ = temperature of injected substance

K= correction factor for specific weight and specific heat of the injected substance and of the blood T= blood temperature t= time;

MTT$_{TDart}$ is mean transit time, and DST$_{TDart}$ is exponential decay time;

and determining a value of a parameter GEDV$_{AT\ TDart}$ which reflects a sum of heart ventricle volumes without lung volume by subtraction according to the equation $$GEDV_{AT\ TDart} = C.\ O._{TDart} - PTV_{TDdart}.$$

13. Process according to claim 12, including the step of determining a value of a parameter PBV$_{TDart}$ which reflects pulmonary blood volume from the equation:

$$PBV_{TDart} = ITBV_{TDart} - GEDV_{AT\ Tdart}$$

where ITBV$_{TDart}$ is intrathoracic blood volume.

14. Process according to claim 13, including the step of determining a value of a parameter EVLW$_{Tdart}$ which reflects extravascular lung water volume from the equation:

$$EVLW_{TDart} = PTV_{TDart} - PBV_{Tart}$$

where PTV$_{TDart}$ is pulmonary thermo-volume.

15. Process according to claim 12, including the step of determining a value of a parameter CFI$_{TDart}$ which reflects a global cardiac function index from the equation:

$$CFI_{TDart} = C.\ O._{TDart}/GEDV_{TDart}$$

16. Process according to claim 12, wherein commencement of the thermo-dilution measurement is initiated by the flow of the cold solution injected.

17. Process according to claim 12, wherein a starting time for determining said circulatory fill status-related parameters is determined from starting and ending times of the cold solution injection.

18. Process according to claim 12, including the steps of determining a time plot of base blood temperature and, extrapolating a base line for the thermo-dilution curve from the time plot.

19. Device for determining a patient's circulatory fill status-related parameters comprising a thermo-dilution measurement arrangement having a thermo-dilution injector fluidically and electronically connected through a temperature sensor and a control and analysis unit to a pulmonary artery catheter and a femoral artery measuring device, wherein output values from the temperature sensor, the catheter and measuring device are directed to the control and analysis unit to generate intrathoracic thermo-volume values ($ITTV_{TDart}$) and pulmonary thermo-volume values ($PTV_{TDart}$) according to the equations:

$$ITTV_{TDdart} = C.O._{Tdart} * MTT_{TDart}$$

$$PTV_{TDdart} = C.O._{TDart} * DST_{TDart}$$

where $C.O._{TDart}$ is cardiac output determined by the control and analysis unit according to the thermo-dilution adapted standard Stewart-Hamilton formula $$C.O. = \frac{V_1 * (T_B T_I) * K}{\int \Delta T dt}$$

and $V_I$=volume of injection $T_B$=blood temperature $T_I$=temperature of injected substance K=correction factor for specific weight and specific heat of the injected substance and of the blood T=blood temperature =time;

$MTT_{TDart}$ is mean transit time, and $DST_{TDart}$ is exponential decay time; and wherein the analysis unit has a difference processor which receives the generated $ITTV_{TDart}$ and $PTV_{TDart}$ values as inputs and which produces an output value $GEDV_{TDart}$ corresponding to a global end-diastolic volume of the heart which reflects the sum of the ventricle volumes without the lung volume.

20. Device according to claim 19, wherein the control and analysis device contains a division processor which receives the cardiac output $C.O._{TDart}$ and the output value $GEDV_{TDart}$ as inputs and which produces a quotient output value which reflects a global cardiac function index.

21. Device for determining a patient's circulatory fill status-related parameters comprising a thermo-dilution measurement arrangement having a thermo-dilution injector fluidically and electronically connected through a temperature sensor to a pulmonary artery catheter and a femoral artery measuring device and a control and analysis device wherein output values from the temperature sensor, the catheter and measuring device generate an appearance time $AT_{TDart}$ and a cardiac output $C.O._{TDart}$ from a thermo-dilution curve of thermo-dilution measurements; wherein lists of values of species-specific characteristics a, b are stored in the analysis device; and wherein the analysis device has a computation element which multiplies the cardiac output $C.O._{TDart}$ by the appearance time $AT_{TDart}$ to obtain a first product, multiplies the first product by a value of species-specific characteristic a from those stored in the analysis device to obtain a second product, adds a value of species-specific characteristic b from those stored in the analysis device to the second product to obtain a resultant, and outputs the resultant as a global end-diastolic volume of the heart $GEDV_{TDart}$ which reflects the sum of the ventricle volumes without the lung volume.

22. Device according to claim 21, wherein lists of values of species-specific characteristics a' and b' are stored in the analysis device, and the analysis device has a computation unit which produces a product by multiplying an accessed value of a' and the resultant $GEDV_{TDart}$ and then adding an accessed value of b' thereto to generate a value of intrathoracic blood volume ITBV.

23. Device according to claim 22, wherein the control and analysis device contains a subtraction unit which processes the value ITBV and the resultant $GEDV_{TDart}$ to produce an output value therefrom which reflects the pulmonary blood volume PBV.

24. Device according to claim 23, wherein the control and analysis device generates a pulmonary thermo-volume value PTV from the thermo-dilution curve and contains a second subtraction unit which processes the values PTV and PBV as input values to produce an output value reflecting an extravascular lung water volume value EVLW.

25. Device according to claim 22, wherein the analysis device generates an intrathoracic thermo-volume value ITTV from the thermo-dilution curve and contains a subtraction unit which processes the values ITTV and ITBV as input values to produce an output value reflecting an extravascular lung water volume value EVLW.

26. Device according to claim 21, wherein an injected-substance flow sensor is fluidically and electronically connected to said pulmonary artery catheter and to said control and analysis unit, to produce an output signal when a substance is injected, thereby generating a time plot for analysis by said control and analysis unit to control the initiation of thermo-dilution measurements.

27. Device according to claim 26, wherein said injected-substance flow sensor comprises a temperature sensor which heats up when the injected substance is stationary.

28. Device according to claim 27, wherein warming means comprising a measurement current associated with said temperature sensor is provided for warming the injected-substance flow sensor.

\* \* \* \* \*